(12) United States Patent
Byrd et al.

(10) Patent No.: US 10,639,004 B2
(45) Date of Patent: May 5, 2020

(54) METHOD AND APPARATUS FOR LOCALIZING AN ULTRASOUND CATHETER

(71) Applicant: St. Jude Medical, Atrial Fibrillation Division, Inc., St. Paul, MN (US)

(72) Inventors: Charles Bryan Byrd, Oakdale, MN (US); Praveen Dala-Krishna, Sicklerville, NJ (US); David A. Jenkins, Sebastian, FL (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 965 days.

(21) Appl. No.: 14/308,221

(22) Filed: Jun. 18, 2014

(65) Prior Publication Data
US 2014/0364719 A1 Dec. 11, 2014

Related U.S. Application Data

(63) Continuation of application No. 13/778,864, filed on Feb. 27, 2013, now abandoned, which is a
(Continued)

(51) Int. Cl.
*A61B 8/14* (2006.01)
*A61B 8/12* (2006.01)
(Continued)

(52) U.S. Cl.
CPC ............... *A61B 8/12* (2013.01); *A61B 5/06* (2013.01); *A61B 5/062* (2013.01); *A61B 5/063* (2013.01);
(Continued)

(58) Field of Classification Search
CPC .. A61B 8/00; A61B 8/463; A61B 8/12; A61B 8/0841; A61B 8/4254; A61B 8/466; A61B 18/14; A61B 18/1492; A61B 2034/105; A61B 2034/2051; A61B 2034/2063
See application file for complete search history.

(56) References Cited

U.S. PATENT DOCUMENTS 3,917,979 A 11/1975 Volk
4,161,121 A 7/1979 Zitelli
(Continued)

FOREIGN PATENT DOCUMENTS

WO WO 2004051571 A2 * 6/2004 ........... G06T 3/0081

OTHER PUBLICATIONS

Dickerson, Keith S., "Comparison of conventional and transverse doppler sonograms", American institute of Ultrasound in Medicine, pp. 497-506, Sep. 1993.
(Continued)

*Primary Examiner* — Baisakhi Roy
(74) *Attorney, Agent, or Firm* — Dykema Gossett PLLC

(57) ABSTRACT

An imaging system is provided with an ultrasound catheter and a controller coupled to the ultrasound catheter. The catheter includes a localizer sensor configured to generate positional information for the ultrasound catheter, and an imaging ultrasound sensor having a restricted field of view. The controller co-registers images from the imaging ultrasound sensor with positional information from the localizer sensor.

16 Claims, 7 Drawing Sheets

Related U.S. Application Data continuation of application No. 12/650,521, filed on Dec. 30, 2009, now Pat. No. 8,428,691, which is a continuation of application No. 10/994,424, filed on Nov. 23, 2004, now Pat. No. 7,713,210.

(51) Int. Cl.
*A61B 5/06* (2006.01)
*A61B 8/00* (2006.01)
*A61B 8/08* (2006.01)

(52) U.S. Cl.
CPC ............ *A61B 5/064* (2013.01); *A61B 8/4254* (2013.01); *A61B 8/4263* (2013.01); *A61B 8/445* (2013.01); *A61B 8/4488* (2013.01); *A61B 8/463* (2013.01); *A61B 8/5238* (2013.01); *A61B 8/54* (2013.01)

(56) References Cited

U.S. PATENT DOCUMENTS

| | | |
|---|---|---|
| 4,241,610 A | 12/1980 | Anderson |
| 4,442,713 A | 4/1984 | Wilson |
| 4,462,408 A | 7/1984 | Silverstein |
| 4,519,260 A | 5/1985 | Fu |
| 4,522,194 A | 6/1985 | Normann |
| 4,534,221 A | 8/1985 | Fife |
| 4,576,177 A | 3/1986 | Webster |
| 4,605,009 A | 8/1986 | Pourcelot |
| 4,841,977 A | 6/1989 | Griffith |
| 4,890,268 A | 12/1989 | Smith |
| 4,917,097 A | 4/1990 | Proudian |
| 4,951,677 A | 8/1990 | Crowley |
| 5,002,059 A | 3/1991 | Crowley |
| 5,090,956 A | 2/1992 | McCoy |
| 5,105,819 A | 4/1992 | Wollschlager |
| 5,139,020 A | 8/1992 | Koestner |
| 5,152,294 A | 10/1992 | Mochizuki |
| 5,156,154 A | 10/1992 | Valenta |
| 5,156,157 A | 10/1992 | Valenta |
| 5,158,087 A | 10/1992 | Gatzke |
| 5,170,793 A | 12/1992 | Takano |
| 5,183,040 A | 2/1993 | Nappholz |
| 5,188,106 A | 2/1993 | Nappholz |
| 5,195,968 A | 3/1993 | Lundquist |
| 5,199,299 A | 4/1993 | Hughes |
| 5,254,088 A | 10/1993 | Lundquist |
| 5,279,559 A | 1/1994 | Barr |
| 5,304,214 A | 4/1994 | DeFord |
| 5,307,816 A | 5/1994 | Hashimoto |
| 5,309,914 A | 5/1994 | Iinuma |
| 5,325,860 A | 7/1994 | Seward |
| 5,336,182 A | 8/1994 | Lundquist |
| 5,345,936 A | 9/1994 | Nishiki |
| 5,345,940 A | 9/1994 | Seward |
| 5,357,550 A | 10/1994 | Asahina |
| 5,358,478 A | 10/1994 | Thompson |
| 5,361,767 A | 11/1994 | Yukov |
| 5,364,351 A | 11/1994 | Heinzelman |
| 5,372,138 A | 12/1994 | Crowley |
| 5,385,148 A | 1/1995 | Lesh |
| 5,395,327 A | 3/1995 | Lundquist |
| 5,438,997 A | 8/1995 | Sieben |
| 5,456,258 A | 10/1995 | Kondo |
| 5,456,664 A | 10/1995 | Heinzelman |
| 5,469,852 A | 11/1995 | Nakamura |
| 5,470,330 A | 11/1995 | Goldenberg |
| 5,470,350 A | 11/1995 | Buchholtz |
| 5,471,988 A | 12/1995 | Fujio |
| 5,499,630 A | 3/1996 | Hiki |
| 5,515,853 A | 5/1996 | Smith |
| 5,515,856 A | 5/1996 | Olstad |
| 5,531,686 A | 7/1996 | Lundquist |
| 5,560,362 A | 10/1996 | Sliwa |
| 5,568,815 A | 10/1996 | Raynes |
| 5,588,432 A | 12/1996 | Crowley |
| 5,615,680 A | 4/1997 | Sano |
| 5,622,174 A | 4/1997 | Yamazaki |
| 5,630,837 A | 5/1997 | Crowley |
| 5,662,116 A | 9/1997 | Kondo |
| 5,697,965 A | 12/1997 | Grifin |
| 5,699,805 A | 12/1997 | Seward |
| 5,701,897 A | 12/1997 | Sano |
| 5,704,361 A | 1/1998 | Seward |
| 5,706,823 A | 1/1998 | Wodlinger |
| 5,713,363 A | 2/1998 | Seward |
| 5,715,817 A | 2/1998 | Stevens-Wright |
| 5,722,403 A | 3/1998 | McGee |
| 5,749,364 A | 5/1998 | Sliwa |
| 5,749,833 A | 5/1998 | Hakki |
| 5,788,636 A | 8/1998 | Curley |
| 5,795,299 A | 8/1998 | Eaton |
| 5,797,848 A | 8/1998 | Marian |
| 5,800,356 A | 9/1998 | Criton |
| 5,803,083 A | 9/1998 | Buck |
| 5,807,324 A | 9/1998 | Griffin |
| 5,810,007 A * | 9/1998 | Holupka ................ A61B 8/08 600/407 |
| 5,840,030 A | 11/1998 | Ferek-Petric |
| 5,842,994 A | 12/1998 | TenHoff |
| 5,846,204 A | 12/1998 | Solomon |
| 5,846,205 A | 12/1998 | Curley |
| 5,853,368 A | 12/1998 | Solomon |
| 5,888,577 A | 3/1999 | Griffin |
| 5,891,088 A | 4/1999 | Thompson |
| 5,906,579 A | 5/1999 | Vander Salm |
| 5,916,168 A | 6/1999 | Pedersen |
| 5,921,978 A | 7/1999 | Thompson |
| 5,928,276 A | 7/1999 | Griffin |
| 5,931,863 A | 8/1999 | Griffin |
| 5,935,102 A | 8/1999 | Bowden |
| 5,938,616 A | 8/1999 | Eaton |
| 5,954,654 A | 9/1999 | Eaton |
| 5,983,123 A * | 11/1999 | Shmulewitz ............ A61B 6/50 128/915 |
| 6,013,072 A | 1/2000 | Winston |
| 6,033,378 A | 3/2000 | Lundquist |
| 6,039,693 A | 3/2000 | Seward |
| 6,085,117 A | 7/2000 | Griffin |
| 6,120,453 A | 9/2000 | Sharp |
| 6,144,870 A | 11/2000 | Griffin |
| 6,149,599 A | 11/2000 | Schlesinger |
| 6,171,248 B1 | 1/2001 | Hossack |
| 6,173,205 B1 | 1/2001 | Griffin |
| 6,190,353 B1 | 2/2001 | Makower |
| 6,192,266 B1 | 2/2001 | Dupree |
| 6,210,333 B1 | 4/2001 | Gardner |
| 6,224,555 B1 | 5/2001 | Schwartz |
| 6,226,028 B1 | 5/2001 | Klein |
| 6,228,032 B1 | 5/2001 | Eaton |
| 6,261,246 B1 | 7/2001 | Pantages |
| 6,293,943 B1 | 9/2001 | Panescu |
| 6,306,096 B1 | 10/2001 | Sweard |
| 6,306,097 B1 | 10/2001 | Park |
| 6,310,828 B1 | 10/2001 | Mumm |
| 6,346,074 B1 | 2/2002 | Roth |
| 6,352,509 B1 | 3/2002 | Kawagishi |
| 6,358,208 B1 | 3/2002 | Lang |
| 6,360,027 B1 | 3/2002 | Hossack |
| 6,368,275 B1 | 4/2002 | Sliwa |
| 6,385,489 B1 | 5/2002 | Griffin |
| 6,398,731 B1 | 6/2002 | Mumm |
| 6,423,002 B1 | 7/2002 | Hossack |
| 6,440,488 B2 | 8/2002 | Griffin |
| 6,443,894 B1 | 9/2002 | Sumanaweera |
| 6,475,148 B1 | 11/2002 | Jackson |
| 6,475,149 B1 | 11/2002 | Sumanaweera |
| 6,482,161 B1 | 11/2002 | Sumanaweera |
| 6,484,727 B1 | 11/2002 | Vaska |
| 6,485,455 B1 | 11/2002 | Thompson |
| 6,490,474 B1 | 12/2002 | Willis |
| 6,491,633 B1 | 12/2002 | Krishnan |
| 6,503,202 B1 | 1/2003 | Hossack |
| 6,517,488 B1 | 2/2003 | Hossack |

(56) References Cited

U.S. PATENT DOCUMENTS

| | | |
|---|---|---|
| 6,527,717 B1 | 3/2003 | Jackson |
| 6,532,378 B2 | 3/2003 | Saksena |
| 6,544,187 B2 | 4/2003 | Seward |
| 6,544,230 B1 * | 4/2003 | Flaherty ............... A61B 17/22 604/164.09 |
| 6,554,770 B1 | 4/2003 | Sumanaweera |
| 6,567,700 B1 | 5/2003 | Turcott |
| 6,589,182 B1 | 7/2003 | Loftman |
| 6,592,520 B1 | 7/2003 | Prskieszyn |
| RE38,209 E | 8/2003 | Yamazaki |
| 6,605,043 B1 | 8/2003 | Dreschel |
| 6,607,488 B1 | 8/2003 | Jackson |
| 6,612,992 B1 | 9/2003 | Hossack |
| 6,645,147 B1 | 11/2003 | Jackson |
| 6,648,875 B2 | 11/2003 | Simpson |
| 6,650,927 B1 | 11/2003 | Keidar |
| 6,654,638 B1 | 11/2003 | Sweeney |
| 6,658,279 B2 | 12/2003 | Swanson |
| 6,690,958 B1 | 2/2004 | Walker |
| 6,690,963 B2 | 2/2004 | Ben-Haim |
| 6,709,396 B2 | 3/2004 | Flesch |
| 6,716,166 B2 | 4/2004 | Govari |
| 6,773,402 B2 | 8/2004 | Govari |
| 6,788,967 B2 | 9/2004 | Ben-Haim |
| 6,908,434 B1 | 6/2005 | Jenkins |
| 6,923,768 B2 | 8/2005 | Camus |
| 6,950,689 B1 * | 9/2005 | Willis ............... A61B 5/0422 128/920 |
| 7,029,467 B2 | 4/2006 | Currier |
| 7,090,639 B2 | 8/2006 | Govari |
| 7,171,257 B2 | 1/2007 | Thomson |
| 7,211,045 B2 | 5/2007 | Dala-Krishna |
| 7,236,821 B2 | 6/2007 | Cates |
| 7,697,972 B2 | 4/2010 | Verard |
| 7,713,210 B2 | 5/2010 | Byrd |
| 2001/0047165 A1 | 11/2001 | Makower et al. |
| 2002/0045810 A1 * | 4/2002 | Ben-Haim ............ A61B 5/0215 600/374 |
| 2002/0115931 A1 * | 8/2002 | Strauss .................... A61B 5/06 600/420 |
| 2003/0045796 A1 | 3/2003 | Friedman |
| 2003/0060700 A1 * | 3/2003 | Solf ...................... A61B 8/0833 600/411 |
| 2003/0158483 A1 | 8/2003 | Jackson |
| 2004/0097805 A1 | 5/2004 | Verard |
| 2004/0138559 A1 * | 7/2004 | Cheng .................. A61B 8/0825 600/437 |
| 2005/0036655 A1 | 2/2005 | Lettvin |
| 2006/0159318 A1 * | 7/2006 | Alyassin ............... G06T 7/0038 382/128 |

OTHER PUBLICATIONS

Sahn, David J., "Advances in ultrasound inaging for congenital heart disease diagnosis and management", Pediatric cardiology—Proceedings of the III world congress of pediatric, Dec. 1, 1989.

Sahn, David J., "Applications for color flow mapping in pediatric cardiology", Cardiology Clinics, pp. 255-264, May 1989.

Sahn, David J., "Important Roles of transeophageal color doppler flow mapping studies in infants with confenital heart disease", Supplement to the Journal of American college of cardiology, vol. 15, No. 2 (Supplement A), Feb. 1990.

Sahn, David J., "Instrumentation and physical factors related to visualization of stenotic and regurgitant jets by doppler color flow mapping", JACC, pp. 1354-1365, Nov. 1988.

Sahn, David J., "Miniaturized high frequency phased array devices for high resolution neonatal and intraoperative imaging", Supplement to journal of the american college of cardiology, vol. 15, No. 2 Supplement A, Feb. 1990.

Sahn, David J., "Phased Arrays for multiplane esophageal echos in infants", Summary statement, Diagnostic Radiology Study Section, Aug. 2, 1990.

Tortoli, Piero et al., "Velocity magnitude estimation with linear arrays using doppler bandwidth", Ultrasounics, pp. 157-161, Apr. 2001.

Vaides-Cruz, Lilliam M., "Experimental Animal Investigations of the potential for new approaches to diagnostic cardiac imaging in infants and small premature infants from intracardiac and trasesophageal approaces using a 20MHz real time ultrasound imaging catheter", Supplement to journal of the american college of cardiology, Feb. 1989.

Valdes-Cruz, Lilliam M., "Transvascular Intracardiac application of miniaturized phase-array ultrasonic endoscope", Brief Rapid Communication, pp. 1023-1027, Mar. 1991.

Wells, P.N.T., "Velocity, absorption and attenuation in biological materials", Biomedical ultrasonics, pp. 110-144, 1977.

* cited by examiner

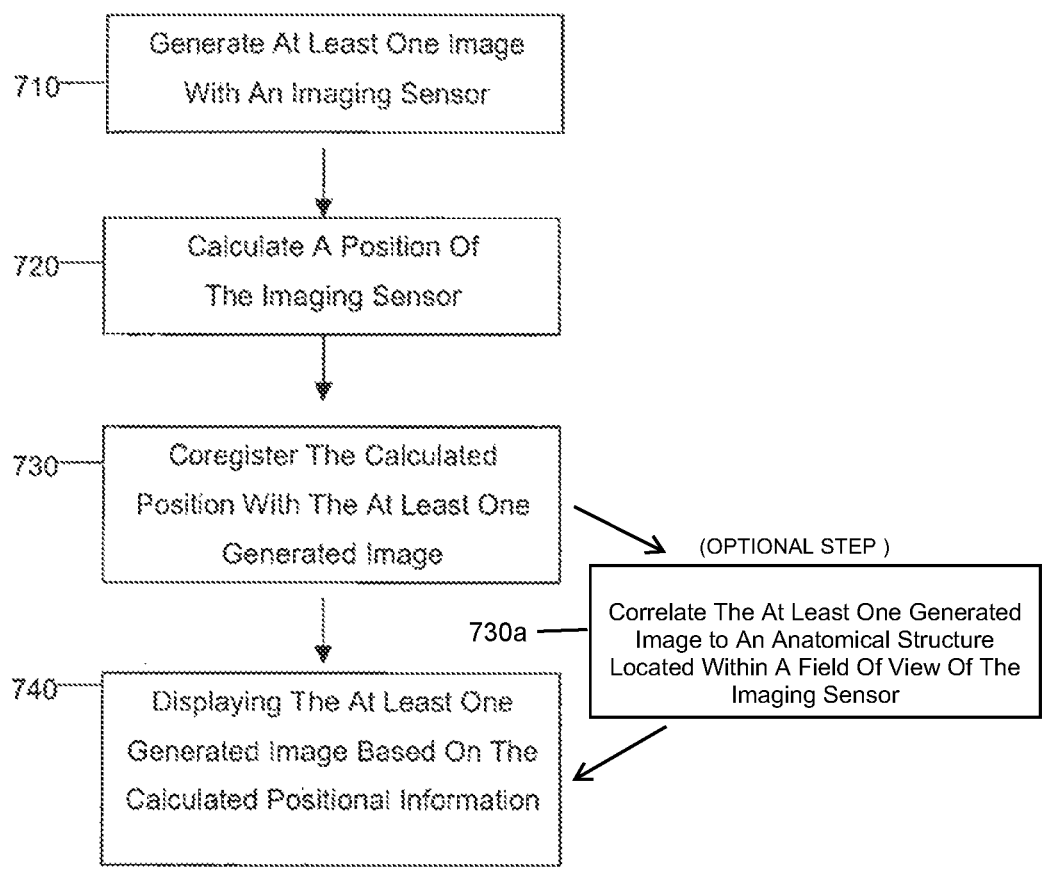

METHOD AND APPARATUS FOR LOCALIZING AN ULTRASOUND CATHETER

CROSS-REFERENCE TO RELATED APPLICATIONS

This application is a continuation of U.S. patent application Ser. No. 13/778,864, filed 27 Feb. 2013 (the '864 application), now pending, which is a continuation of U.S. patent application Ser. No. 12/650,521, filed 30 Dec. 2009 (the '521 application) now U.S. Pat. No. 8,428,691, issued 23 Apr. 2013, which is a continuation of U.S. patent application Ser. No. 10/994,424, filed 23 Nov. 2004 (the '424 application) now U.S. Pat. No. 7,713,210, issued 11 May 2010. The '864 application, the '521 application and the '424 application are each hereby incorporated by reference in their entirety as though fully set forth herein.

BACKGROUND OF THE INVENTION

1. Field of the Invention

The present invention relates generally to medical imaging systems, and more particularly to a method and apparatus for localizing an ultrasound imaging catheter.

2. Description of the Related Art

Medical imaging technology is used to improve the diagnosis and treatment of medical conditions. Presently available medical imaging technology includes a wide variety of ultrasound, X-ray, nuclear, magnetic resonance imaging (MRI) and other imaging systems. A technology of particular benefit to diagnosis and treatment of cardiovascular conditions uses imaging ultrasound detectors mounted a percutaneous catheter.

Techniques exist for localizing catheters deployed within a patient's body. One such technique is described in U.S. Pat. No. 6,192,266 to Dupree ("Dupree" hereafter), which is incorporated by reference herein in its entirety. In particular, Dupree generates an electric field with one of a basket electrode and a roving electrode, the electric field being characterized by the physical dimensions and spacing among the basket electrodes. A navigation application is provided which analyzes the spatial variations in the electrical potentials sensed within the field, and provides a location output which locates the roving electrode within the space defined by the basket, in terms of its position relative to the position of the multiple basket electrodes. Other such systems also exist.

The Dupree system, however, may be problematic in some applications due to its use of an electrode generated electric field to determine the location of the probe. In particular, electric fields generated intra-body can generate electrical currents which flow in the body that may cause muscle stimulation, which may result in heart arrhythmias, etc., when used in or near the heart, such as intra-cardiac sensing or treatment. Thus, a need exists for a non-electric field-based catheter locating system that does not induce significant electric currents in the body. There is also a particular need for catheter locating methods that are compatible with ultrasound imaging catheters, and for methods of utilizing localized position information in combination with image rendering.

Other problems with the prior art not described above can also be overcome using the teachings of the present invention, as would be readily apparent to one of ordinary skill in the art after reading this disclosure.

SUMMARY OF THE INVENTION

According to an embodiment of the present invention, an imaging system is provided with an ultrasound catheter including a tubular body, and a controller coupled to the ultrasound catheter. The ultrasound catheter includes a localizer sensor adapted and configured to generate positional information for the ultrasound catheter, and an imaging ultrasound sensor positionable relative to the tubular body so as to have a first restricted field of view. The controller co-registers images from the imaging ultrasound sensor with positional information from the localizer sensor. Preferably, the first restricted field of view spans less than 360 degrees about the tubular body.

According to another embodiment of the present invention, a method of displaying medical images from a catheter-based imaging ultrasound sensor having a first restricted field of view is provided including generating at least one image with the imaging ultrasound sensor, calculating a position of the imaging ultrasound sensor, coregistering the calculated position with the at least one generated image, and displaying the at least one generated image based on the calculated positional information, wherein the first restricted field of view spans less than 360 degrees about a body of the catheter.

According to another embodiment of the present invention, an imaging system is provided including means for generating a plurality of two dimensional (2D) images of a structure, means for determining a section of the structure corresponding to each of the plurality of 2D images, and means for displaying a three dimensional (3D) display of at least a portion of the structure from the plurality of 2D images.

BRIEF DESCRIPTION OF THE DRAWINGS

FIG. 7 depicts a method of displaying medical images from a catheter-based imaging sensor having a restricted field of view according to another embodiment of the present invention.

DETAILED DESCRIPTION OF THE EXEMPLARY EMBODIMENTS

Figure 1A:
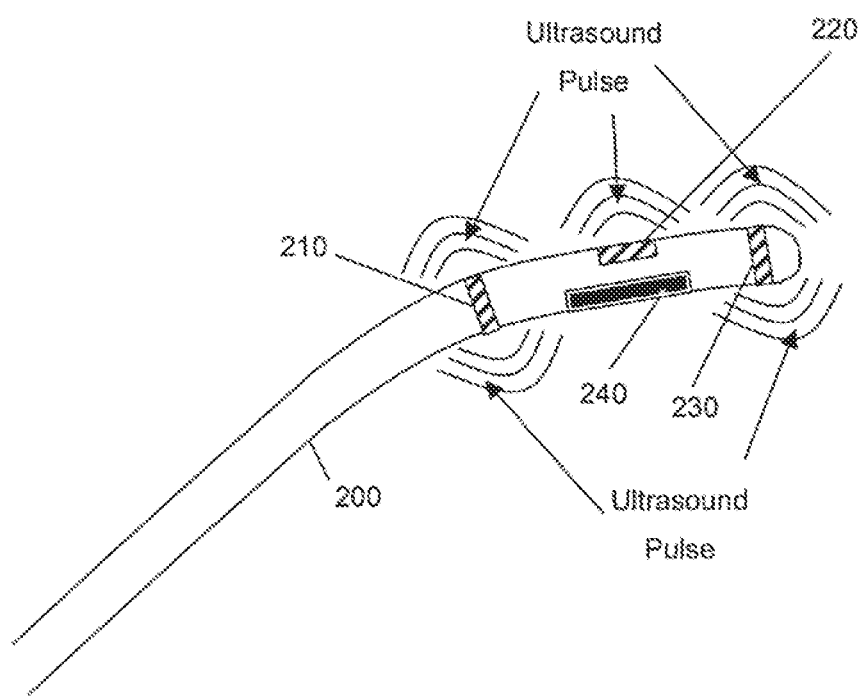
FIG. 1A depicts an ultrasound catheter probe according to an embodiment of the present invention.

Reference will now be made in detail to exemplary embodiments of the present invention. Wherever possible, the same reference numbers will be used throughout the drawings to refer to the same or like parts.

The various embodiments of the present invention provide capabilities to determine the location of medical instrumentation and/or treatment devices within a patient's body using ultrasound echolocation and/or three dimensional (3D) triangulation techniques, and to use this localized information in conjunction with medical images. Relative positions of one instrument with respect to other instruments and registration of instrumentation positions with respect to the patient's body may be obtained, which is generally referred to herein as "localizing" the instrumentation. Thus, references to catheters as particular types of medical instrumentation and treatment devices are not intended to be limiting since the claimed systems and methods equally apply to other non-catheter probes/medical devices positional within the body, including remote or robotic surgery, esophageal probes, and medical, veterinarian and forensic applications where an instrumentation or tools require positioning within a body where they cannot be observed directly by the operator.

The various embodiments of the present invention employ sensors on a probe, such as a catheter, that are capable of sensing a signal to determine a range or bearing to an emitter in combination with 1, 2, 3 or more emitters in order to determine a one-dimensional (1D), two-dimensional (2D) or three-dimensional (3D) position, respectively, of the probe with respect to the emitters. The range or bearing information is referred to herein as positional information because the information permits determining the position of the sensor with respect to an emitter and/or a frame of reference. The sensors that receive signals from emitters are referred to herein as localizer sensors, because the sensors permit locating the sensor with respect to an emitter and/or a frame of reference. Three types of ranging/directional signals described herein include magnetic fields, electrical fields and ultrasound, but other signals are contemplated consistent with the purpose and techniques described herein. The emitters may be placed on or within a body, preferably at dispersed positions around and near an area in which the probe will be operated.

As will be discussed, the emitters are preferably positioned at predetermined, fixed or determinable (i.e., measurable) positions on, in or near the body to provide a relative frame of reference for locating the probe. When the positions of emitters are based upon the patients body, such as on the chest at measured distances from a part of the anatomy (e.g., the sternum), the emitters provide a relative frame of reference for positioning the probe with respect to the body. Also, emitters may be positioned at predetermined or measured locations with respect to an external or absolute frame of reference, such as an operating table or electrophysiology lab. When the positions of emitters are measured against an external frame of reference, they are said to be "registered" to the external frame of reference and may serve as fiducial references for locating the probe within the external frame of reference.

Magnetic field emitters may be used to localize a probe within a patient's body by using magnetic field sensors positioned on the probe, such as a catheter to measure the magnetic field strength or sense a direction of the magnetic field. In this embodiment, magnetic field emitters are magnets of a known or measurable field strength, such as permanent magnets and electromagnets. Preferably, electromagnets are used so that the emitted magnetic field can be turned on and off sequentially to permit sensors to determine a range or bearing to each electromagnet sequentially.

In an embodiment employing magnetic field strength measurements, a magnetic field strength sensor is positioned at a known or fixed position on a probe, such as a catheter, that is capable of measuring the relative or absolute magnetic field around it. Since the strength of a magnetic field decreases with distance from a magnet, a range or distance to the magnet from the sensor can be calculated using known methods and simple calculations. By measuring the range $R_i$ to three or more magnets, a 3D position of the sensor is easily calculated using well known methods as the intersection of three or more spheres of radius $R_i$ each centered on each magnet.

In an alternative embodiment employing magnetic field direction sensors, a magnetic field direction sensor is positioned at a known or fixed position on a probe, such as a catheter, that is capable of sensing the direction of a local magnetic field. Similar to a compass, this sensor may be configured to sense the direction or bearing to the magnet in 1, 2 or 3 dimensions with respect to the catheter. By measuring the bearing to three or more magnets, a 3D position of the sensor is easily calculated using well known triangulation methods as the intersection of three or more vectors each passing through a magnet.

Electric field emitters may be used to localize a probe within a patient's body by using electric field sensors positioned on the probe, such as a catheter to measure the electric field strength or other electric field properties such as impedance. In such embodiments, an electric field may be applied to the body by means of an electrode to which a voltage or alternating field (such as radio frequency) is applied of a known or measurable strength. The electric field applied to electrodes can be turned on and off sequentially to permit sensors to determine a range to each electrode sequentially.

In an embodiment employing electric field sensors, a voltage sensor, such as an electrode, is positioned at a known or fixed position on a probe, such as a catheter, that is capable of measuring the relative electric (i.e., voltage) field around it. Since the strength of an electric field decreases with distance from an electrode, a range or distance to the magnet from the sensor can be calculated using known methods and simple calculations. By measuring the range $R_i$ to three or more magnets, a 3D position of the sensor is easily calculated using well known methods as the intersection of three or more spheres of radius $R_i$ each centered on each magnet.

In an alternative embodiment employing electric field sensors, a electric field sensor, such as an electrode, is positioned at a known or fixed position on a probe, such as a catheter, that is capable of receiving an alternating electric field and passing the signal, such as via a coaxial cable, to external equipment configured to measure impedance between the emitter electrode and the sensor electrode on the catheter. Since the impedance between the electrode emitter and sensor electrode on the catheter varies with distance, a range or distance to the emitter electrode can be calculated using known methods and simple calculations. Similar to other embodiments, by measuring the range $R_i$ to three or more electrodes, a 3D position of the sensor is easily calculated using well known methods as the intersection of three or more spheres of radius $R_i$ each centered on each electrode.

Ultrasound emitters may be used to localize a probe within a patient's body by using ultrasound sensors positioned on the probe, such as a catheter to measure receive ultrasound pulses emitted by emitters positioned within or external to the body.

According to such an embodiment of the present invention as shown in FIG. 1A, an ultrasound catheter 200 includes an imaging ultrasound sensor 240, and a positional array with positional sensors 210, 220, 230. Preferably, positional sensors 210, 220, 230 comprise ultrasound sensors as will be described in greater detail below. Other positional sensors are also contemplated, such as the magnetic positional sensors and resistance/impedance positional sensors described above, as would be readily apparent to one of ordinary skill in the art after reading this disclosure.

A first annular ultrasound sensor 230 may be positioned at or near a proximal end of the catheter 200 and second annular ultrasound sensor 210 may be positioned at some distance from the first annular ultrasound sensor 230. In this embodiment, the first annular ultrasound sensor 230 and the second annular ultrasound sensor 210 are positioned so as to bracket the imaging ultrasound sensor 240 along a length of the catheter 200.

Figure 1B:
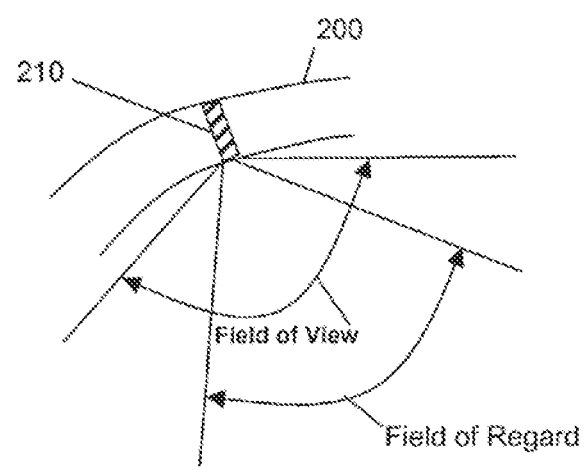
FIG. 1B depicts a field of regard and a field of view for one side of one of the ultrasound sensors of FIG. 1A.

As referenced above, the term "annular" refers to sensors which have a "field of view" that extends substantially all the way around the long axis of the catheter 200. Magnetic, electric and ultrasound sensors may each be configured as annular sensors Annular ultrasound sensors are typically ring shaped transducers that create ultrasound pulses and receive echoes from those pulses around the circumference of the catheter 200. Due to their configuration, annular ultrasound sensors may create and/or receive minimal or no ultrasound pulses along the length (i.e., long axis) of the catheter 200 (see FIG. 1B, which shows a restricted field of view with no ultrasound pulses being created/received along the length of the catheter 200). An annular ultrasound sensor may comprise a single sensor, such as a ring-shaped transducer, or an array of sensors.

In addition to annular ultrasound sensors 210, 230, a directional sensor 220 may be circumferentially positioned at a known angle about the catheter axis relative to the imaging ultrasound sensor 240. Preferably, the known angle between the directional sensor 220 and the imaging ultrasound sensor 240 is in the range of about 90 degrees to about 180 degrees. Most preferably, the known angle is about 180 degrees around the catheter circumference from the transmission face of the imaging ultrasound sensor 240. In the exemplary embodiment illustrated in FIG. 1A, the directional sensor 220 is positioned substantially opposite the imaging ultrasound sensor 240 about the catheter 200. Other configurations are also contemplated.

As referenced above, the term "directional" refers to sensors which do not transmit or which do not have a field of view that extends substantially all the way around the long axis of catheter 200. Due to this configuration, directional ultrasound sensors, for example, create and/or receive ultrasound pulses along a restricted field of view (i.e., a field of view less than 360 degrees about the long axis of catheter 200). Such a field of view may be cone-shaped where the angle of the cone of transmitted and/or received ultrasound may narrow to nearly 180 degrees. However, the breadth of the restricted field of view may vary depending on the particular directional sensor 220 utilized, as would be readily apparent to one of ordinary skill in the art after reading this disclosure.

It should be appreciated that while only three ultrasound sensors 210, 220, 230 are shown as forming the positional ultrasound array, additional sensors may also be provided to improve the accuracy and/or reliability of the position determination as would be readily apparent to one of ordinary skill in the art after reading this disclosure. By way of example, a near-omni directional transducer may be mounted on a tip of catheter 200; e.g. a transducer which has a 4.pi. radians (approximate) field of view except along the length of catheter 200 (i.e., the long axis). This near-omni directional transducer may be substituted for or be provided in addition to the annular ultrasound sensors 210, 230.

It should also be appreciated that ultrasound has a limited path length within the body due to sound absorption by tissue and blood, and therefore more than three sensors may be required in some applications to localize medical devices positioned near or beyond the maximum path length of the particular tissue. Further, in addition to the limited path length issue, multipath issues can also be problematic in ultrasound based localizers. Multipath refers to ultrasound pulses generated by a first source arriving at first receiver at different times due to different path lengths. The speed of ultrasound is different in bones, tissues, and fluids (e.g., blood). Thus a single ultrasound pulse passing through different body structures will arrive at a sensor at slightly different times. Also, ultrasound may refract in, reflect off and preferentially conduct through different body structures, permitting an ultrasound pulse to reach a sensor along different paths. The combined effects are multipath errors that may reduce location accuracy achievable with ultrasound localization because determination of the travel time of an ultrasound pulse does not correlate exactly to the distance traveled. However, by providing more than three sensors, the combined distance measurements can be correlated to help reduce multipath induced errors.

Additionally, one or more of ultrasound sensors 210, 220, 230 may be positioned on a rigid portion of catheter 200, and/or one or more of ultrasound sensors 210, 220, 230 may be positioned on a flexible portion of catheter 200. Preferably, at least imaging ultrasound sensor 240 and directional ultrasound sensor 220 are positioned on a rigid portion of catheter 200. Other configurations are also contemplated. For example, with catheters that may be flexed or bent in one or more angles, additional sensors (e.g., one for each positionable segment) may be used to provide 3D position information on the catheter segments.

Figure 2:
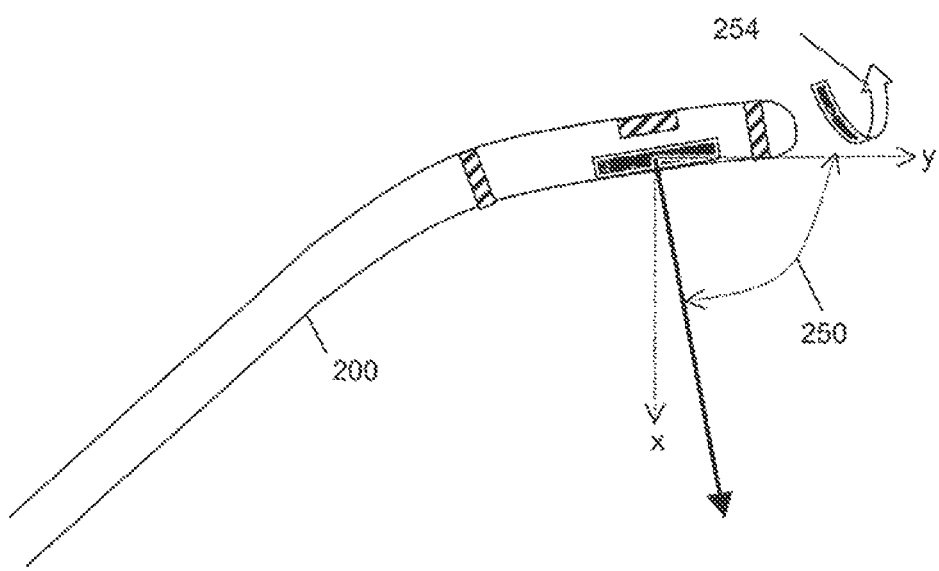
FIG. 2 depicts a yaw angle and a roll of the ultrasound catheter probe of FIG. 1A.
Figure 3:
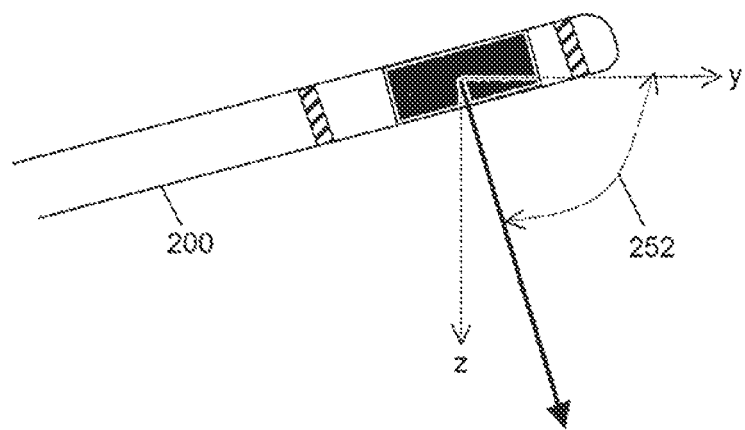
FIG. 3 depicts a pitch angle of the ultrasound catheter probe of FIG. 1A.

As shown in FIGS. 2 and 3, the ultrasound pulses of the first annular ultrasound sensor 230 and the second annular ultrasound sensor 210 are used to determine the 3D position of the catheter 200 with respect to a frame of reference. As discussed above, it should be appreciated that the phrase "frame of reference" refers to any known position and/or coordinate system which can be used to determine the absolute position of catheter 200 within a patient's body by knowing the relative position between the frame of reference and the catheter 200 and the relative position of the patient's body and the frame of reference. In this regard, the frame of reference may be established using a second or third catheter (see FIG. 4) having a known position or an image obtained by other technology (e.g., fluoroscopy, x-ray, etc.). The frame of reference may be a fixed frame of reference to which the catheters and the patient are located (e.g., on an exam table or the like), a frame of reference fixed on the patient's body (e.g., externally generated ultrasound signals provided at registered fiducial points on the patient's body), a detected and recognizable structure (e.g., the heart wall or valve). The use of a frame of reference is also applicable to embodiments using non-ultrasound positional sensors, such as the magnetic positional sensors, and resistance/impedance positional sensors previously described. It should be appreciated that multiple frames of reference may be used to further improve the accuracy and reliability of the position determination, the selection of which may depend upon the nature of the medical procedure and the required positional precision.

According to the present embodiment, the ultrasound pulses generated by the first annular ultrasound sensor 230 and the second annular ultrasound sensor 210 as well as the echoes in response thereto are measured (in time and/or strength) and are used to determine the planar angle 250 along the X-Y plane (the "yaw" angle) and the Z offset angle 252 (the "pitch" angle) with respect to the frame of reference using positioning algorithms known in the art. For example, knowing the speed of sound in blood and the time when a pulse is emitted, the measured delay of a received pulse can be used to determine position by spherical triangulation. It should be appreciated that increasing the number of annular ultrasound sensors 210, 230 as previously noted would improve accuracy of the pitch and yaw determination, as more relational data is generated for the positioning algorithms.

In addition to determining the 3D position of the catheter 200, it is also desirable to know the direction an instrument, such as an ultrasound imaging transducer, optical imager or microsurgical instrument, is facing. For example, interpretation of intracardiac echocardiography images would be facilitated if the direction that the imaging ultrasound sensor 240 is facing is known with respect to the frame of reference, particularly for an imaging ultrasound sensor 240 with a limited field of view. This determination can be achieved by receiving in some but not all catheter sensors the ultrasound pulse generated by directional ultrasound sensor 220 as well as the echo off other sensors (in time and/or strength) and the pulses from those other catheter sensors within the field of view of directional ultrasound sensor 220, the data from which is collectively used to calculate the direction the directional ultrasound 220 is pointed. As directional ultrasound sensor 220 is positioned at a known angle from the ultrasound sensor 240 about the catheter 200, the direction 254 of ultrasound sensor 240 (the "roll" of catheter 200) relative to the frame of reference can be determined based on the measured direction of directional ultrasound sensor 220.

The aforementioned configuration thus has the capability of determining the 3D position of the catheter 200 relative to the frame of reference, as well as the direction of imaging ultrasound sensor 240. This provides a user of the system with a greater amount of information as to the position of a given image generated by catheter 200 than in conventional systems. In particular, various embodiments provide the user with the pitch, yaw, and roll position of catheter 200 having an imaging ultrasound sensor 240 with a restricted field of view. Thus a six dimensional (6D) (x, y, z, pitch, yaw, roll) localizing capability is afforded by embodiments of the present invention.

Figure 4:
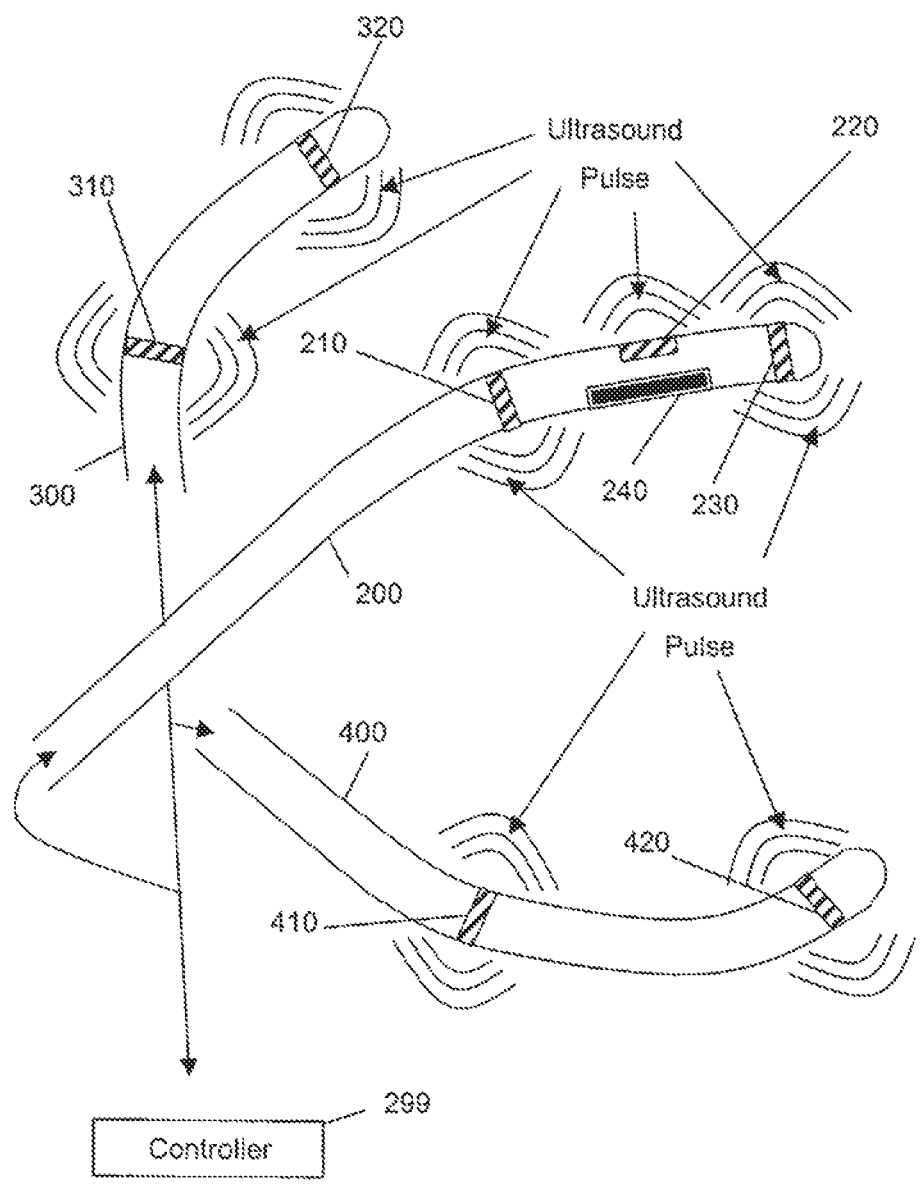
FIG. 4 depicts a positioning system according to an embodiment of the present invention.

According to another embodiment of the present invention as shown in FIG. 4, a catheter positioning system is provided for more accurately determining the position (or relative position) of catheter 200 of FIG. 1A. In particular, the catheter positioning system includes a first positioning catheter 300 and a second positioning catheter 400 preferably positioned at some angle from catheter 200 as shown. By way of example, if the catheter 200 is used for intracardiac ultrasound (and thus positioned somewhere in the right atrium of a patient's heart), the first positioning catheter 300 and second positioning catheter 400 may be positioned so as to better triangulate the position of the catheter 200 within the heart. Other locations for positioning catheters 300, 400 are also contemplated. Additionally, an external location source/system, such as an X-ray system and/or external ultrasound transducers/beacons, may be used in conjunction with the aforementioned configuration to better determine or to confirm the position of ultrasound catheter 200. The position of one or both of catheters 300, 400 may be established by an external localizing means (e.g., an x-ray), so as to qualify as a frame of reference for determining the position of catheter 200. This embodiment may be used to reduce x-ray exposure to the patient and attendants by using one or a few x-ray images to localize the positioning catheters 300, 400, which then can be used to localize the imaging catheter 200 during an intracardiac echocardiography session without the case of additional fluoroscopy. Alternatively, additional or other frames of references may also be used as previously described.

According to the exemplary embodiment shown in FIG. 4, the first positioning catheter 300 includes at least two annular localizer sensors 310, 320 positioned on a tubular body thereof so as to generate respective near-omni directional ultrasound pulses. In a like manner, the second positioning catheter 400 includes at least two annular localizer sensors 410, 420 positioned on the tubular body thereof so as to generate respective near-omni directional ultrasound pulses. The positional sensors 310, 320, 410, 420 illustrated in FIG. 4 comprise ultrasound sensors, however non-ultrasound sensors may also be used, such as the magnetic positional sensors, and resistance/impedance positional sensors previously described. The annular ultrasound sensors 310, 320, 410, 420 of the positioning catheters 300, 400 can be similar to the annular ultrasound sensors 210, 230 of catheter 200 in that they create and/or receive ultrasound pulses from substantially all angles about the circumference of catheters 300, 400, respectively. Other configurations are also contemplated, such as positioning catheters each with only one annular ultrasound sensor, positioning catheters each with more than two annular ultrasound sensors, and configurations with only one positioning catheter or more than two positioning catheters.

Figure 6:
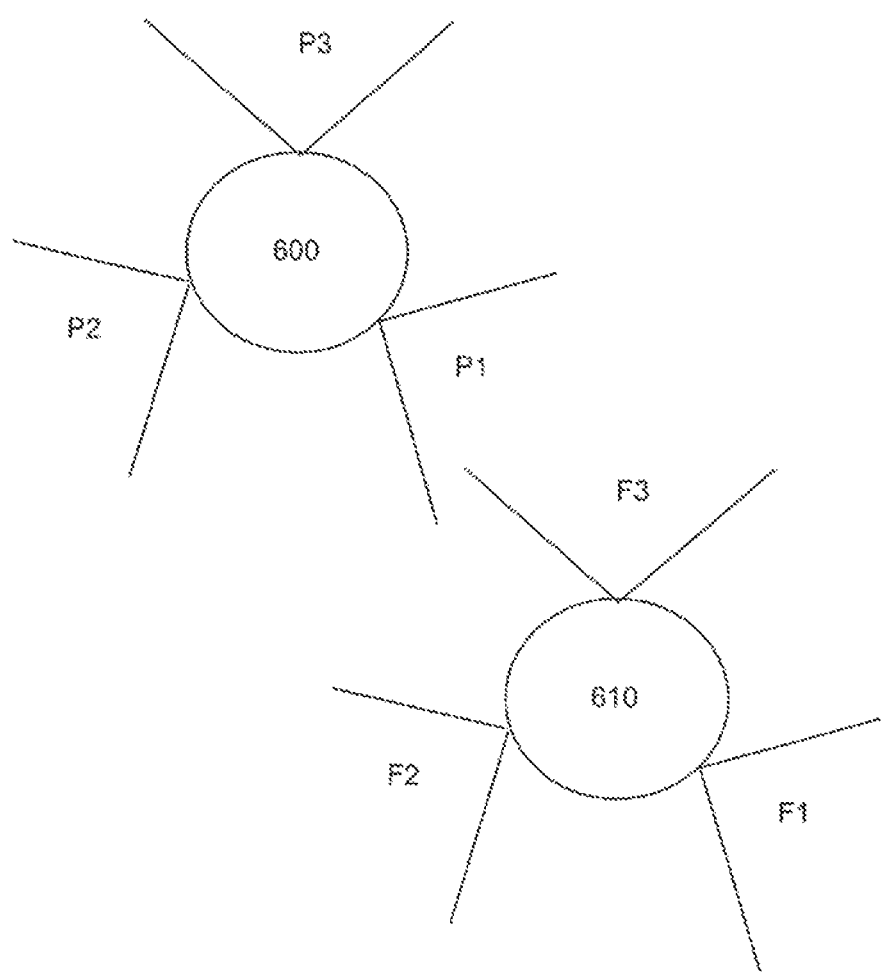
FIG. 6 depicts a cross sectional view of catheter probes including a plurality of directional sensors according to another embodiment of the present invention.

Alternatively, instead of annular sensors, two, three, four or more directional ultrasound sensors may be spaced at known angular intervals to provide near-omni directional ultrasound pulses. This alternative embodiment may further feature using different ultrasound frequencies on each such directional sensor or pulsing such sensors at different known times so that received pulses can be processed to identify which of the directional sensors emitted the received pulse. This additional information may be useful in certain applications where multipath errors may be an issue or where high positional precision is required (e.g., when microsurgery is being performed). An exemplary implementation of this technique is shown in greater detail in FIG. 6, with catheters 600, 610 generating a plurality of ultrasound pulses from directional sensors having individual field of views P1, P2, P3 (for catheter 600) and F1, F2, F3 (for catheter 610). Other configurations are also contemplated.

It should be appreciated that, while ultrasound positional sensors have been described, other non-ultrasound positional sensors may be used. As previously noted, examples of non-ultrasound positional sensors include magnetic positional sensors and resistance/impedance positional sensors. It should further be appreciated that a combination of the ultrasound and non-ultrasound positional sensors may be used for some applications. Such a combination may be used for positioning catheter 300, positioning catheter 400, and/or catheter 200.

According to another embodiment of the present invention, the positioning catheters 300, 400 and the ultrasound catheter 200 are electrically coupled to controller 299, the controller 299 being adapted and configured to receive the echo data and to determine therefrom a three dimensional (3D) position of the ultrasound catheter 200 relative to a frame of reference from electrical signals generated by positioning catheters 300, 400 and ultrasound catheter 200. The controller 299 may comprise an appropriately programmed microprocessor, an application specific integrated circuit (ASIC) or other similar control and calculation device, as would be readily apparent to one of ordinary skill in the art after reading this disclosure.

According to an embodiment of the present invention, the positioning catheters 300, 400 and the ultrasound imaging catheter 200 are coupled to controller 299 via an integrated positioning and imager junction box. The integrated positioning and imager junction box may include isolation circuitry to reduce or eliminate stray currents from controller 299, which would otherwise be radiated along the length of catheter 200.

In operation, the annular ultrasound sensors 310, 320 of first positioning catheter 300, the annular ultrasound sensors 410, 420 of second positioning catheter 400, and the annular ultrasound sensors 210, 230 of ultrasound catheter 200 record the time of arrive of pulses from all positioning sensors in their field of regard. Additionally, echoes of a given sensor's own pulses bouncing off another catheter may also be received and used to determine location. For example, an imaging ultrasound sensor may image a catheter within its field of view. As such, the field of view and field of regard of a given sensor may differ, where the "field of regard" refers to the direction(s) from which a given sensor may receive echoes (see FIG. 1B). Hence, the field of regard may be the same or different from a given sensor's overall field of view, which is the directions in which the sensor is facing.

Using the known speed of sound through blood, the controller 299 is able to calculate the relative positions of the sensors by spherical triangulation. More specifically, the ultrasound sensors 310, 320 detect the ultrasound sensors 210, 230, 410, 420; the ultrasound sensors 210, 230 detect the ultrasound sensors 310, 320, 410, 420; and the ultrasound sensors 410, 420 detect the ultrasound sensors 310, 320, 210, 230. By measuring the time delay of each pulse and/or the signal strength of received pulses, the relative positions of the three catheters 200, 300 and 400 can be determined using known algorithms, and thus used to calculate the pitch and yaw of catheter 200 relative to the frame of reference.

To further determine the roll of catheter 200, the annular ultrasound sensors 310, 320 of catheter 300, the directional ultrasound sensor 220 of catheter 200, and the annular ultrasound sensors 410, 420 of catheter 400 detect each other. Thus, the ultrasound sensors 310, 320 detect the ultrasound sensors 220, 410, 420; the directional ultrasound sensor 220 detects the ultrasound sensors 310, 320, 410, 420; and the ultrasound sensors 410, 420 detect the ultrasound sensors 310, 320, 220. By measuring the time delay of each pulse and/or the signal strength of received pulses, the relative positions of directional ultrasound sensor 220 from ultrasound sensors 310, 320, 410, 420 can be determined using known algorithms. In this regard, it should be appreciated that not all of ultrasound sensors 310, 320, 410, 420 may detect the directional ultrasound sensor 220 due to the restricted field of view of directional ultrasound sensor 220. However, based off of the measured time delay and/or signal strength of the received pulses (including a measurement of no pulse received), the direction of directional ultrasound sensor 220 can be determined. This allows the direction of imaging ultrasound sensor 240 to be determined based on the known angle between imaging ultrasound sensor 240 and directional ultrasound sensor 220.

The aforementioned location technique can be enhanced by gating each of the ultrasound sensors 310, 320, 210, 220, 230, 410, 420 to operate or emit pulses at different time intervals. Alternatively, each of the ultrasound sensors 310, 320, 210, 220, 230, 410, 420 may operate at different frequencies (preferably also different from imaging ultrasound sensor 240), such that multiple ones of the ultrasound sensors 310, 320, 210, 220, 230, 410, 420 may generate/detect simultaneously. In this manner, the identity of each positioning sensor can be easily determined by the controller 299 according to the received frequency. Other configurations and methods are also contemplated.

Figure 5:
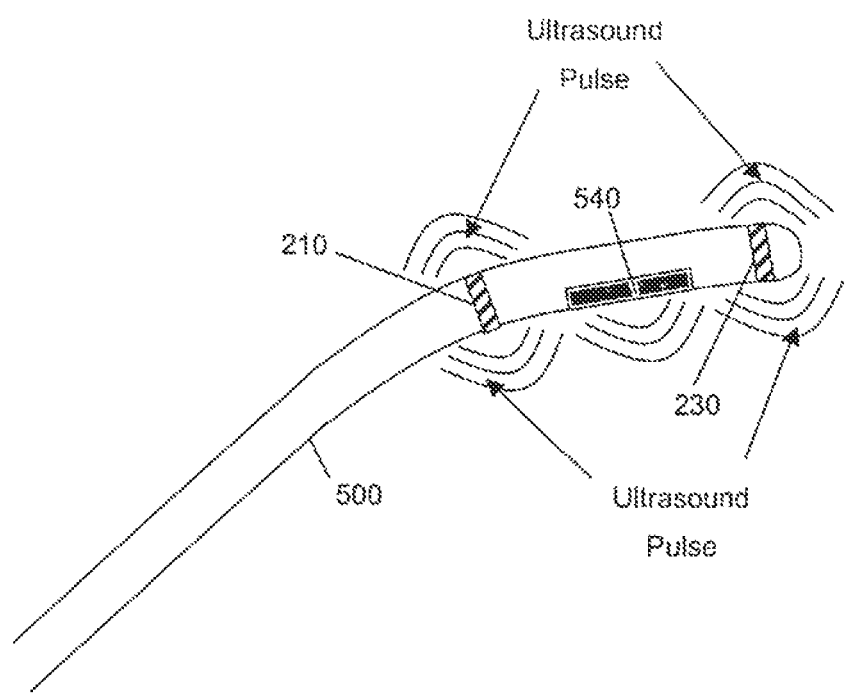
FIG. 5 depicts an ultrasound catheter probe according to another embodiment of the present invention.

According to an embodiment of the present invention as shown in FIG. 5, an ultrasound imaging catheter 500 is provided, the ultrasound catheter including an imaging ultrasound sensor 540, and a positional ultrasound array with positional ultrasound sensors 210, 230. Similar to the ultrasound catheter 200 of FIG. 1A, first annular ultrasound sensor 230 is positioned at or near a proximal end of the catheter 200 and second annular ultrasound sensor 210 is positioned at some distance from first annular ultrasound sensor 230. Preferably, the first annular ultrasound sensor 230 and the second annular ultrasound sensor 210 are positioned so as to bracket the imaging ultrasound sensor 540 along a length of the catheter 500.

While the ultrasound catheter 500 of FIG. 5 is similar to ultrasound catheter 200 of FIG. 1A, the ultrasound catheter 500 utilizes one or more of the transducer elements of the imaging ultrasound sensor 540 in positioning determination rather than or in addition to a directional sensor 220 as with catheter 200. In this regard, imaging ultrasound sensor 540 may be configured to operate in at least a positioning mode during which the imaging ultrasound sensor 540 generates and/or receives a positioning ultrasound pulse, and an imaging mode during which the imaging ultrasound sensor 540 generates and/or receives an imaging ultrasound pulse. The ultrasound catheter 500 may be configured to have imaging ultrasound sensor 540 only operate in the positioning mode when the ultrasound catheter 500 is moved or on command by a user thereof, or may be configured to periodically operate in the positioning mode for periodic updates of the position.

The aforementioned technique can be performed by pulsing one or more single elements individually (e.g., one on each end of a linear array), by pulsing a plurality of elements together (e.g., non-phased), or by forming a directional pulse via phasing the pulses of each element (which may or may not include directing the direction pulse at specific positional sensors). Due to the high frequency of ultrasound and the high scan rate of a linear phased array ultrasound transducer, periodic localizing pulses may be transmitted so frequently that the positioning mode appears to be operating simultaneously with the imaging mode without noticeably degrading the quality of images.

The embodiment illustrated in FIG. 5 eliminates the need for a directional ultrasound sensor 220. Thus, the present embodiment benefits from a reduced cost.

It should be appreciated that the particular frequency of a given ultrasound sensor for any one of the embodiments shown in FIGS. 1-6 may be selected based on the precision and penetration depth required. Thus, for ultrasound sensors positioned outside the body (e.g., sensors used as extra-body fiducials) a lower frequency may be selected, in order to achieve a higher degree of penetration depth. For an ultrasound imaging sensor, such as sensor 240 in FIG. 1A, a higher frequency may be selected, in order to achieve a higher degree of precision. Thus, particularly for ultrasound sensors positioned intra-body, higher frequencies are typically used than for ultrasound sensors positioned outside the body. Other configurations and methods are also contemplated.

According to another embodiment of the present invention, the positioning information from any one of the aforementioned embodiments may be used in control equipment to assist the operator in positioning and operating an ultrasound imaging catheter. Specifically, a rectangle or other shape representing the field of regard of the imaging sensor may be projected onto a 3D (e.g., wire-frame, cartoon or stylized) representation of the patient's heart rendered on a display device to show the operator the portion of the patient's body that is or will be imaged based upon the present position and orientation of the sensor. The image generated by the imaging ultrasound sensor 240, 540 and positional information may be correlated to heart structures within the 3D wire-frame image (or stylized image) of an idealized heart using known image processing techniques. Once the ultrasound image provided by the ultrasound imaging catheter 200 has been correlated to heart structures, and the 3D wire-frame image (or stylized image) has been correlated to those heart structures, the catheter localizer information and ultrasound image can be applied to the 3D wire-frame image (or stylized image) to graphically depict the image including the location of all (or some) catheters within the heart for easier interpretation by the user. This embodiment provides the operator with more visual information, and thus a more easily understood representation of the position of the ultrasound catheters 200, 500 and the image generated thereby. Specifically, a 3D wire-frame image may be transparent, allowing the operator to "see" the catheter(s) positions relative to the heart structures. This may be particularly useful in procedures where catheters are used to precisely position electrodes on the heart wall based upon real-time images provided by an intracardiac ultrasound imaging catheter since the positions of all catheters relative to the heart are displayed for the physician.

According to another embodiment of the present invention, the localizer information can be used in conjunction with images obtained from catheter 200. By way of example, one such process is described in copending application entitled "Method and Apparatus for Time Gating of Medical Images", filed currently with the present application and incorporated by reference herein in its entirety. Another such process is shown in the flowchart of FIG. 7, and described in greater detail below.

As shown in FIG. 7, at least one embodiment of the present invention includes methods of displaying medical images from a catheter-based imaging sensor having a restricted field of view, such as a two dimensional (2D) ultrasound imaging sensor. In step 710, the imaging sensor is used to generate at least one image (preferably 2D) of a structure of interest. In step 720, a position of the imaging sensor is calculated, and then coregistered in step 730 with the at least one image generated in step 710. This may include, for example, an optional step 730a of correlating or coregistering a section of the structure of interest (e.g., a heart) with at least one image generated in step 710.

In step 740, the at least one generated image of step 710 is displayed based on the calculated positional information from step 720. By way of example, step 740 may include displaying a 3D model of the structure of interest, and then highlighting a section of the 3D model of the structure of interest which corresponds to the coregistered section of step 730. Preferably, the 3D model is generally depicted in a first color or colors, and the highlighted section is depicted in a second color different from the first color(s). Other configurations are also contemplated.

The foregoing description of various embodiments of the invention has been presented for purposes of illustration and description. It is not intended to be exhaustive or to limit the invention to the precise form disclosed, and modifications and variations are possible in light of the above teachings or may be acquired from practice of the invention. The embodiments were chosen and described in order to explain the principles of the invention and its practical application to enable one skilled in the art to utilize the invention in various embodiments and with various modifications as are suited to the particular use contemplated.

What is claimed is:

1. A medical apparatus for co-registering x-ray and ultrasound images, comprising:
a controller adapted to couple to an ultrasound imaging catheter and an x-ray imaging source, the controller configured to:
establish a frame of reference with the x-ray imaging source;
determine a location of the ultrasound imaging catheter within the frame of reference;
receive an x-ray image containing the ultrasound imaging catheter and a tissue surrounding the ultrasound imaging catheter;
receive at least one ultrasound image of the tissue from the ultrasound imaging catheter;
co-register the x-ray image with at least one ultrasound image from the ultrasound imaging catheter;
generate on a display device a graphical representation including the x-ray image from the x-ray imaging source, the at least one ultrasound image from the ultrasound imaging catheter, and a visual indicator corresponding to the co-registration of the x-ray image with the at least one ultrasound image;
generate a model of a geometry of an anatomical structure and highlight one or more features on the model corresponding to a location for which the at least one ultrasound image has been captured by the ultrasound imaging catheter; and
generate a spatial representation of a field of view of the ultrasound imaging catheter onto the model, wherein the spatial representation indicates a portion of the anatomical structure that is or will be imaged based upon the location of the ultrasound imaging catheter.

2. The medical apparatus of claim 1, wherein the visual indicator indicates that the at least one ultrasound image is co-registered with the x-ray image.

3. The medical apparatus of claim 2, wherein the visual indicator comprises a highlighted section of interest of the tissue.

4. The medical apparatus of claim 1, wherein the controller is further configured to co-register at least one additional image from a second imaging catheter.

5. The medical apparatus of claim 1, wherein the controller is further configured to correlate the at least one ultrasound image to an anatomical structure located within a field of view of the ultrasound imaging catheter.

6. A method for imaging tissue within the body of a patient, comprising:
establishing a frame of reference with an x-ray imaging source;
determining a location of an ultrasound imaging catheter within the frame of reference;
receiving from the x-ray imaging source an x-ray image containing the ultrasound imaging catheter and a tissue surrounding the ultrasound imaging catheter;
receiving from the ultrasound imaging catheter at least one ultrasound image of the tissue;
co-registering the x-ray image with the at least one ultrasound image from the ultrasound imaging catheter;
outputting to a display device a graphical representation including the x-ray image, the at least one ultrasound image, and a visual indicator corresponding to the co-registration of the x-ray image with the at least one ultrasound image;

generating a model of a geometry of an anatomical structure and highlighting one or more features on the model corresponding to a location for which the at least one ultrasound image has been captured by the ultrasound imaging catheter;

displaying the highlighted model on the display device; and projecting a spatial representation of a field of view of the ultrasound imaging catheter onto the model, wherein the spatial representation indicates a portion of the anatomical structure that is or will be imaged based upon the location of the ultrasound imaging catheter.

7. The method of claim 6, wherein the visual indicator indicates that the at least one ultrasound image is co-registered with the x-ray image.

8. The method of claim 7, wherein the visual indicator comprises a highlighted section of interest of the tissue.

9. The method of claim 6, further comprising correlating the at least one ultrasound image to an anatomical structure located within a field of view of the ultrasound imaging catheter.

10. A system for co-registering x-ray and ultrasound images of a patient's body, the system comprising:
    a field emitter configured to generate an electrical field within the body;
    an ultrasound imaging catheter, comprising:
        an elongate body including a proximal section and a distal section;
        at least one annular ultrasound imaging sensor disposed on the distal section of the elongate body and configured to image tissue within a field of view surrounding the ultrasound imaging catheter; and
        a plurality of positional sensors configured to sense the electrical field generated by the field emitter; and
    a controller adapted to couple to the field emitter, the ultrasound imaging catheter, and an x-ray imaging source, wherein the controller is configured to:
        establish a frame of reference with the x-ray imaging source;
        determine a location of each of the plurality of positional sensors within the frame of reference;
        receive an x-ray image containing the ultrasound imaging catheter and the tissue surrounding the ultrasound imaging catheter;
        receive at least one ultrasound image of the tissue from the ultrasound imaging catheter;
        co-register the x-ray image with the at least one ultrasound image from the ultrasound imaging catheter;
        output the x-ray image and the at least one ultrasound image to a display device;
        generate a model of a geometry of an anatomical structure and highlight one or more features on the model corresponding to a location for which the at least one ultrasound image has been captured by the ultrasound imaging sensor; and
        project a spatial representation of a field of view of the ultrasound imaging catheter onto the model, wherein the spatial representation indicates a portion of the anatomical structure that is or will be imaged based upon the location of the ultrasound imaging catheter.

11. The system of claim 10, wherein the controller is further configured to generate on the display device a visual indicator corresponding to the co-registration of the x-ray image with the at least one ultrasound image.

12. The system of claim 10, wherein the controller is further configured to project onto the display device a three-dimensional position of the ultrasound imaging catheter.

13. The system of claim 10, wherein the controller is further configured to correlate the at least one ultrasound image to an anatomical structure located within the field of view.

14. The system of claim 10, wherein the at least one ultrasound imaging sensor comprises a phased-array transducer.

15. The system of claim 10, wherein the field emitter comprises an external magnetic field emitter, and wherein the positional sensors are magnetic positional sensors.

16. The system of claim 10, wherein the field emitter comprises an external electric field emitter, and wherein the positional sensors are resistive or impedance positional sensors.

* * * * *